(12) United States Patent
Tucker-Schwartz et al.

(10) Patent No.: US 10,788,413 B2
(45) Date of Patent: Sep. 29, 2020

(54) METHOD TO DISTINGUISH AND ANALYZE WHITE BLOOD CELLS IN THE PRESENCE OF RED BLOOD CELLS

(71) Applicant: Massachusetts Institute of Technology, Cambridge, MA (US)

(72) Inventors: Jason Michael Tucker-Schwartz, Cambridge, MA (US); Shivang R. Dave, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/399,172

(22) Filed: Jan. 5, 2017

(65) Prior Publication Data
US 2018/0188151 A1    Jul. 5, 2018

(51) Int. Cl.
| | | |
|---|---|---|
| G01N 15/14 | (2006.01) | |
| C12Q 1/04 | (2006.01) | |
| G01N 33/49 | (2006.01) | |
| G01N 15/00 | (2006.01) | |
| G01N 15/10 | (2006.01) | |

(52) U.S. Cl.
CPC .......... *G01N 15/1436* (2013.01); *C12Q 1/04* (2013.01); *G01N 15/1434* (2013.01); *G01N 15/1459* (2013.01); *G01N 33/492* (2013.01); *G01N 33/4915* (2013.01); *G01N 2015/008* (2013.01); *G01N 2015/0073* (2013.01); *G01N 2015/1006* (2013.01); *G01N 2015/1488* (2013.01)

(58) Field of Classification Search
CPC ........... G01N 15/1436; G01N 33/4915; G01N 33/492; G01N 2015/0065; G01N 2015/0073; G01N 2015/008; G01N 2015/035; G01N 2015/006; G01N 2015/1081; G01N 15/14; G01N 2015/1488; G01N 2015/149; G01N 21/05
See application file for complete search history.

(56) References Cited

U.S. PATENT DOCUMENTS 4,745,279 A * 5/1988 Karkar .................. G01N 21/05
250/343
5,408,326 A * 4/1995 Wang ................... G01N 21/255
250/576

(Continued)

FOREIGN PATENT DOCUMENTS

| | | |
|---|---|---|
| WO | 2016/050755 A2 | 4/2016 |
| WO | 2016/142785 A1 | 9/2016 |

OTHER PUBLICATIONS

Solen, Kenneth, et al. "Light-scattering instrument to detect thromboemboli in blood." Journal of Biomedical Optics 8.1 (2003): 70-80.*

(Continued)

*Primary Examiner* — Shawn Decenzo
(74) *Attorney, Agent, or Firm* — Nutter McClennen & Fish LLP

(57) ABSTRACT

Method for distinguishing between red blood cells and white blood cells. The method includes obliquely illuminating the blood sample with light from at least two rotational angles and analyzing light side scattered from cells in the sample to provide accurate discrimination of white blood cell types based on the anisotropy of red blood cell side scatter as compared to more isotropic white blood cell side scatter.

32 Claims, 2 Drawing Sheets

(56) References Cited

U.S. PATENT DOCUMENTS

| | | | |
|---|---|---|---|
| 9,772,282 B2 | 9/2017 | Tucker-Schwartz et al. | |
| 2008/0019887 A1* | 1/2008 | Lohmann | G01N 21/05 422/243 |
| 2008/0317325 A1 | 12/2008 | Ortyn et al. | |
| 2010/0273168 A1* | 10/2010 | Krockenberger | G01N 15/00 435/6.12 |
| 2013/0308122 A1 | 11/2013 | Merchez et al. | |
| 2014/0030696 A1* | 1/2014 | Luscher | G01N 15/1404 435/3 |
| 2014/0295536 A1* | 10/2014 | Yamada | G01N 15/1436 435/288.7 |
| 2016/0061821 A1* | 3/2016 | Tateyama | G01N 21/49 435/6.1 |

OTHER PUBLICATIONS

[No Author Listed] No-lyse, no-wash assays for the Attune NxT Acoustic Focusing Cytometer. Bioprobes, Journal of Cell Biology Applications. Jun. 1, 2015, vol. 71, pp. 28-30.
International Search Report and Written Opinion for Application No. PCT/US2017/025836, dated Sep. 26, 2017 (16 Pages).

* cited by examiner $\Omega_{LED1} = \Omega_{LED2}$

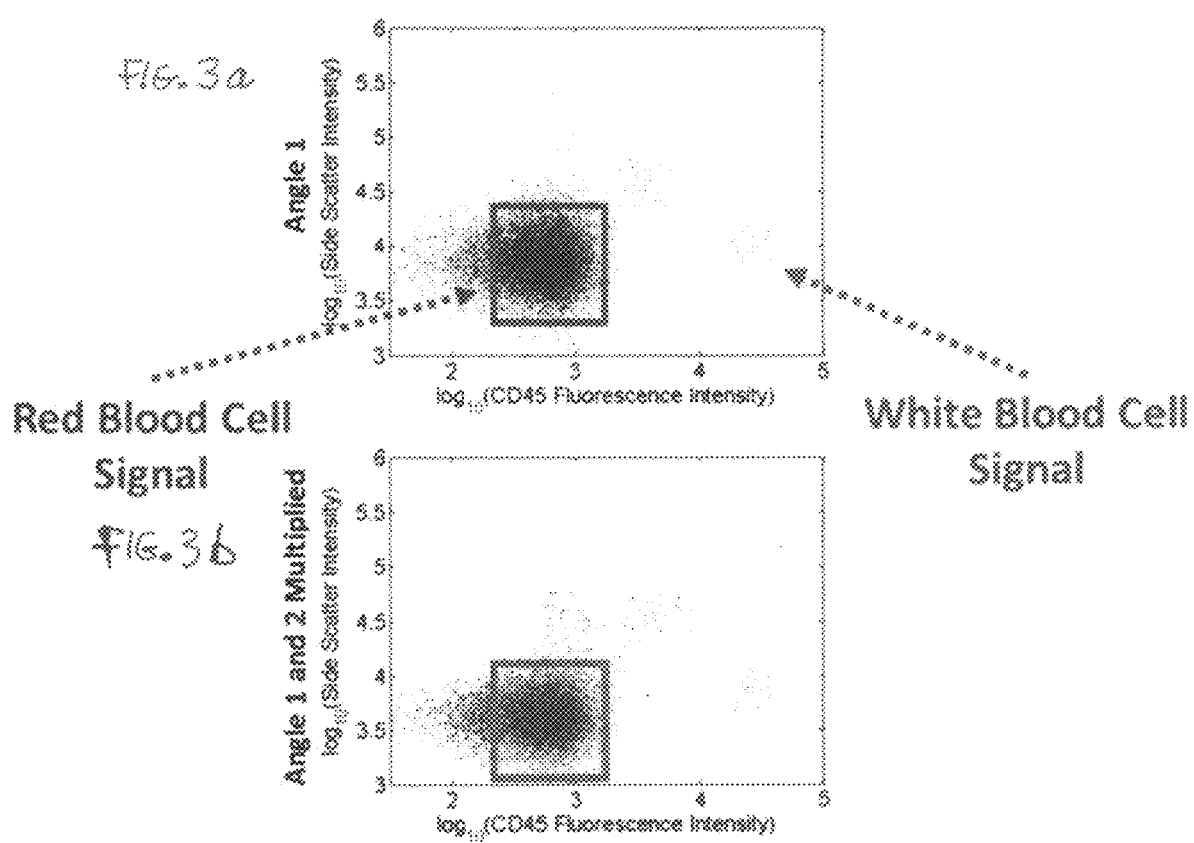

METHOD TO DISTINGUISH AND ANALYZE WHITE BLOOD CELLS IN THE PRESENCE OF RED BLOOD CELLS

This invention was made with Government support under Grant No. U54 EB015403 awarded by the National Institutes of Health. The Government has certain rights in the invention.

BACKGROUND OF THE INVENTION

This invention relates to a method for analyzing, at low magnification, white blood cells in the presence of red blood cells that does not require lysing of the red blood cells.

Of paramount importance in a clinical setting is the analysis of blood and bone marrow samples. Specifically in clinics and hospitals, analysis of patient blood and marrow samples is used to diagnose or rule out a vast number of conditions. In 2014, there were 41.5 million complete blood counts and automated differential white blood cell counts combined performed in the USA. Of central importance to this test is the analysis and discrimination of white blood cell types by flow cytometers and hematology analyzers. Analyzing white blood cell types and counts gives insight to the clinician into immune system status, general health, or clues for diagnosis. However, hematology analyzers and flow cytometers fail to accurately analyze white blood cells in the presence of significant red blood cell numbers. Red blood cells can be mistaken for white blood cells, infiltrate the white blood cell measurement, or any number of other errors that can make the analysis of a sample inaccurate. This is the reason that red blood cells are often lysed (or destroyed) when white blood cells are to be analyzed. Lysing red blood cells allows for more reliable analysis of white blood cells in the patient's blood. A primary concern in sample analysis is the incomplete lysis of red blood cells. Red blood cells can be resistant to lysis in a large population of patients including those with liver disease, sickle cell disease, those undergoing chemotherapy, and in newborns to name a few. Because the red blood cells become difficult to lyse, the samples must be re-run or analyzed manually via a peripheral blood smear.

An object of the invention is a method that can be added to an image based cytometer or hematology analyzer to reduce the impact of red blood cells on the analysis of white blood cells and allow for more accurate assessment of the white blood cell population. This invention can also be used to increase measurement accuracy in cases where a lyse-free measurement is used in clinical devices, which currently is not common.

SUMMARY OF THE INVENTION

The method according to the invention for distinguishing between red blood cells and white blood cells in a flowing or stationary blood sample including red and white blood cells includes obliquely illuminating the blood sample with light from at least two rotational angles. Light side scattered from cells in the sample is analyzed to provide accurate discrimination of white blood cell types for white blood cell analysis and counting based on a difference in light scattering profile of red blood cell side scatter as compared to white blood cell side scatter. In a preferred embodiment the difference in scattering profile is the relative difference in isotropy/anisotropy for the red blood cells and white blood cells. In a preferred embodiment, the oblique illumination angle is approximately 80 degrees. A suitable range is 78-86 degrees. In another preferred embodiment the rotational angles are 90 degrees. A suitable rotational angle range is 75-105 degrees. In this embodiment, the light has a wavelength anywhere in the ultraviolet-visible-near infrared electromagnetic spectrum. A suitable light wavelength is approximately 400 nm.

We thus disclose a set of methods to accurately analyze white blood cells in the presence of red blood cells, specifically for applications in hematology analysis. The method distinguishes blood types by illuminating a flowing or stationary blood sample from multiple angles and analyzing the light interaction with each cell. Embodiments of this invention can be used for imaging based analysis (low resolution or high resolution alike) of flowing or stationary cells on a surface. This method works for any sample containing red and/or white blood cells (e.g. bone marrow, peripheral blood) and can be used in samples with hard-to-lyse red blood cells or in samples without any lysis of red blood cells. This could also be applied to any cell types discussed within this disclosure. Since this method relies on scattering-based contrast, it does not require dyes, although incorporating existing dye, fluorescence, scattering, absorption, etc. methods with the one presented here could aid in its accuracy.

BRIEF DESCRIPTION OF THE DRAWING

FIG. 3a is a graph of side scatter intensity versus CD45 flourescence intensity for a red blood cell.

FIG. 3b is a graph of side scatter intensity for angle 1 and angle 2 versus CD45 flourescence intensity.

DESCRIPTION OF THE PREFERRED EMBODIMENT

Figures 1A, 1B:
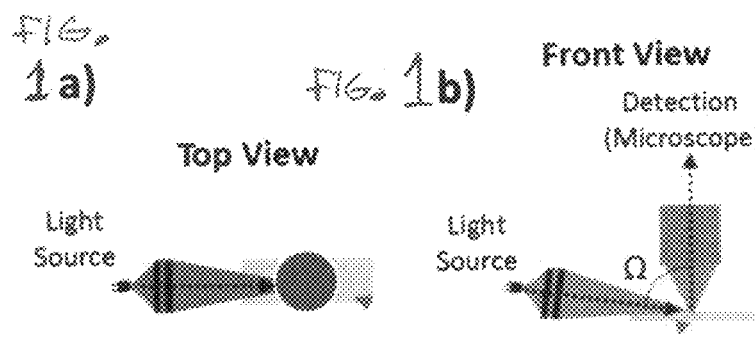
FIG. 1a is a top view of an embodiment of the side scatter imaging technique disclosed herein.
FIG. 1b is a front view of an embodiment of the side scatter imaging technique disclosed herein.

Of particular interest in this invention is the wide angle scatter of light by cells. When light interacts with a cell, one of the possibilities is for the light to be deflected to any number of angles. When the light is deflected a wide or large angle (>5 degrees, most often centered at 90 degrees) away from the original axis, this can often be used to measure the internal complexity of a cell. In flow cytometry and hematology analyzers, this angle is often centered around 90 degrees and referred to as side scatter. Side scatter measurements from white blood cells can aid in discriminating white blood cell types, an essential task in almost any analysis of blood in the clinical or research setting. Side scatter can be used in conjunction with forward scatter, fluorescence, light absorption, or any number of analysis methods to distinguish types of white blood cells or discriminate white blood cells from other blood constituents. When many red blood cells are present, the side scatter signal from red blood cells in the flow path or image plane can create false positive white blood cell-like signals or make measurements of nearby white blood cells inaccurate. The disclosed technology consists of a modular optical add-on to image based analyzers (or slit based cytometers) and analysis methods that can attenuate the effects of red blood cells and aid in accurate quantification of white blood cell signals and thus better discrimination of white blood cell types.

The technology disclosed herein uses the differences in the source of side scatter signal for white blood cells and red blood cells, and the directional anisotropy of the scatter found in red blood cells to distinguish background red blood cells from the white blood cells of interest. In previous literature, these observations have never been made or leveraged to differentiate the two cell types.

The invention disclosed herein describes a set of optical instrumentation and analysis methods that allow for white blood cells to be more accurately analyzed in the presence of un-lysed or hard-to-lyse red blood cells. The technology theories suggested here can be applied to imaging-based solutions to hematology analysis that use high or low resolution microscopy to image flowing samples or stationary cell samples on a surface. It can also be applied to slit-based cytometers that do not supply 2-dimentional images but still supply sub-cellular feature resolution.

The basis of the technology disclosed herein leverages wide angle "side" scatter commonly employed by flow cytometry, and also highly oblique illumination microscopy for image based methods. In hematology analyzers and flow cytometers, wide angle scatter is one method used to help differentiate cell types by their internal complexity, and can be one of a subset of angles collected by a hematology analyzer. Other methods to discriminate cell type include impedance, low and forward angle scatter, absorption by a dye, fluorescence, high resolution imaging, etc. However, nearby red blood cells can pollute the measurement of a white blood cell making its measurement inaccurate, or be misconstrued as white blood cells by the majority of these measurement types. Our technology limits this effect and better discriminates and analyzes white blood cells by leveraging the anisotropy of red blood cell side scatter and more isotropic white blood cell side scatter. Also, because the technology in this patent application utilizes scatter-based measurements, it can be employed on label-free samples, although additional labels can certainly aid in better discrimination of cell groups.

Figure 1C:
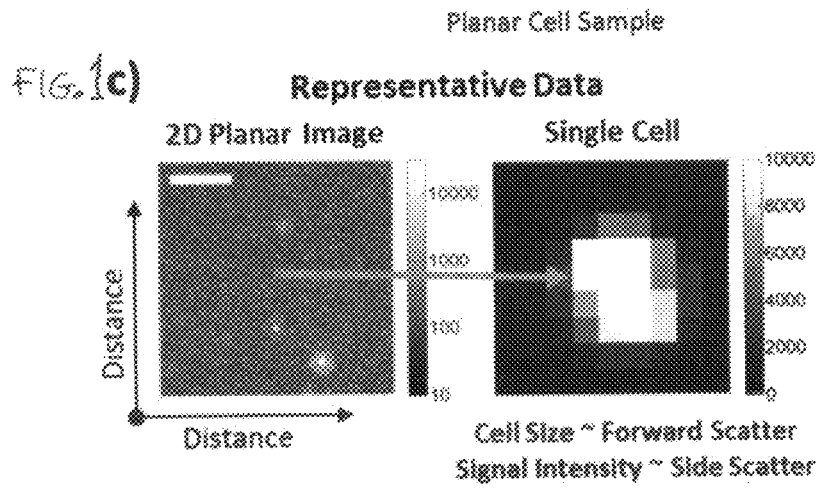
FIG. 1c constitutes representative data from experiments using the disclosed methodology.

The optical embodiment of this technology begins with a setup similar to highly oblique illuminators for scatter-based discrimination of cells in a planar microscopy setting (FIGS. 1a, 1b and 1c). Any form of imaging detection scheme can be used (high/low resolution, high/low numerical aperture, upright/inverted detection configuration, etc.) that can image cells that are flowing in single file, as a group, or stationary cells on a surface. A highly oblique illuminator that allows for side scatter data to be collected from all of the cells in the field of view is mounted adjacent to a microscope detection path at an angle $\Omega$ as shown in FIGS. 1a and 1b. The illuminator and detector can have any number of numerical apertures, but a low numerical aperture illuminator is more practical for homogenous illumination. The angle $\Omega$ between the illuminator and detecting microscope can be any number of angles, but we have found highly oblique angles approaching 80 degrees allow for homogenous side scatter signal over a wide field of view with minimal concern of imaging lens working distance. In FIG. 1a a highly oblique illuminator is placed next to a planar sample that is positioned underneath a microscope imaging objective as shown. At low magnification, many cells can be imaged, and the size of the cell and signal intensity of the cell can be used to differentiate white blood cell types. At low magnification, many cells can be imaged, and the size of the cell and signal intensity of the cell can be used to differentiate white blood cell types. At high magnification, the spatial features of the cells can be used to differentiate white blood cells. The wavelength of the illuminator can fall anywhere in the ultraviolet-visible-near infrared electromagnetic spectrum. Wavelengths where peak red blood cell absorption occurs due to hemoglobin (~400 nm for example) are preferred as they allow for better separation of red blood cell and white blood cell signals.

Figure 2A:
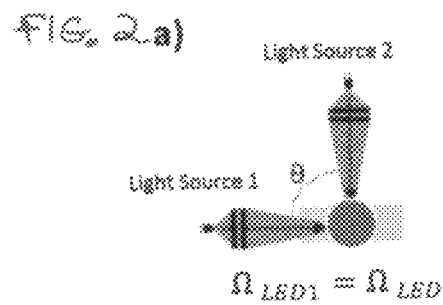
FIG. 2a is a schematic illustration showing the use of two light sources in an embodiment of the invention.
Figure 2B:
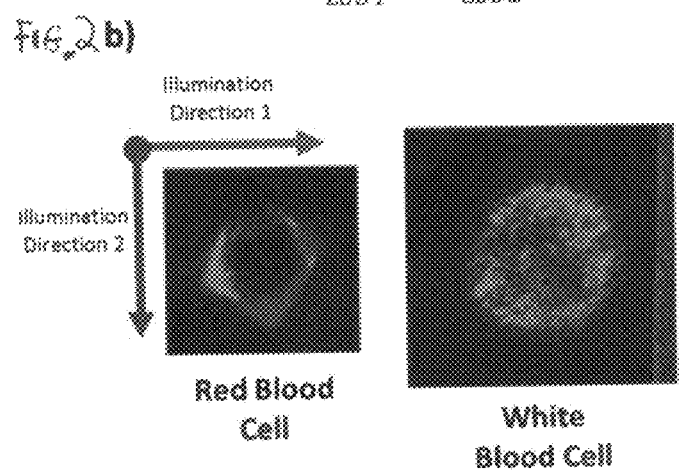
FIG. 2b constitutes photomicrographs of a red blood cell and a white blood cell observed using the technology of the invention.

In white blood cells, the primary source of side scatter is internal granularity and structure of a specific spatial periodicity. This source of contrast exists to a fairly constant amount and from a similar spatial position within the cell regardless of the incoming illumination's rotational angle with respect to the sample and detection axis. Red blood cells, however, have a side scatter signal that originates primarily from refractive index mismatches with the surrounding fluid. This means that the source of the red blood cell side scatter signal becomes focused at the entry and exit sides of illumination. Therefore, illuminating at two distinct rotational angles causes changes in the resulting image (due to spatial changes in where the detected signal originates from the cell). In imaging based cytometry (i.e. highly oblique illumination microscopy as in FIGS. 1a and 1b), this is easily visible as focused spots at two opposing directions on the circular edge of the red blood cell. In FIG. 2a we have added a second oblique illuminator that has the same angle of incidence on the sample (i.e. $\Omega1=\Omega2$), but the second illuminator has been rotated $\theta=90$ degrees around the detection axis of the system. The two rotationally offset illuminators were sequentially used to image a white blood cell and a red blood cell under 40× magnification (FIG. 2b), and the detected imaging information was overlaid and color coded by blue and purple pixels depending on the direction of illumination. It is clear that the two color channels (i.e. the two illumination directions) significantly overlap spatially in the white blood cell due to the internal granularity structure being the source of contrast whereas for red blood cells the refractive index mismatch at the edges causes concentrated signals only along the axis of illumination.

The observed differences in response (signal/image) under two rotationally offset angles of illumination is the method to differentiate cell types. Although the 40× image shows features that should distinguish between white blood cell and red blood cell types, most analyzers operate at lower magnification to increase throughout, and when red blood cells and white blood cells are physically touching, separating the signals is a different task. Using multi-angle illumination can aid in attenuating the effects of red blood cells that overlap with neighboring white blood cells. Note that this idea does not hold only for two illuminators rotationally offset by 90 degrees. This preferred embodiment allows for the greatest difference of mutual information between images for red blood cells in our experience, but any number of illuminators greater than or equal to 2 and any angular offset could potentially lead to better detection of white blood cells and attenuation of red blood cell signal. It is important to note that although this disclosure has been described in the context of wide angle scatter ($\Omega$ approaching 90 degrees from the detection axis), the idea works for any side angle of illumination, so long as the illumination is rotated perpendicular to the detection axis. We have chosen very wide angle scatter since there is a long history of side scatter being used to distinguish white blood cell types. Therefore, using very wide angle scatter allows for discriminating white blood cells from red blood cells as well as differentiating white blood cell types. That does not mean, however, that other angles of interrogation (e.g., Ω=5 degrees) are not incorporated into this idea.

The optical embodiment of this disclosure allows for distinct images with differing interrogating angles for the varying highly oblique or side scatter illuminators. A further analysis step then uses the information from the two or more images to:
a) attenuate the effects of red blood cells on further analysis of cells present in the sample (e.g., white blood cells)
b) better identify only white blood cells for further analysis (e.g., have a better delineation of the white cell boundary within the image)
c) better analyze white blood cells (e.g., better interrogate pixels on the sensor that correspond to the white blood cell and not the red blood cell).

This can be achieved in any number of ways, some of which are listed below as a number of varying embodiments. The following analysis embodiments are examples and includes any form of publicly available analysis that utilizes the information from more than one angle of highly oblique or side scatter illumination is covered by this application.

One way to attenuate the effects of the red blood cells on image analysis is to combine the information from the two or more images from different illumination angles that leverages the high degree of mutual information for the white blood cell images and the low degree of mutual information for the red blood images. For example, multiplying the two images together will attenuate out the red blood cell signal relative to the white blood cell. Since the signals do not overlap significantly in two dimensional space, the red blood cell signal is greatly attenuated, while the white blood cell signal remains due to significant spatial overlap of the two images. The images can be blended or fused using any number of methods (e.g., multiplication, addition, subtraction, weighted combination operations, combination of manipulations, etc.) to reduce the effect of red blood cells, and we have found that multiplying the images is quite effective and elegant. This can be especially advantageous for removing imaging partial volume effects of red blood cell and white blood cells nearby to one another.

One can then do any number of analysis methods on the high or low magnification image and better segment and analyze the white blood cells. For low magnification images, cell event detection using linear discriminant analysis models followed by 2-dimensional Gaussian fitting for each cell event using an expectation maximization model that accounts for background signal has proven a very effective method to quantify size and side scatter intensity that can be used to later differentiate white blood cell types. The effect of attenuating the red blood cells is shown in FIGS. 3a and 3b. For this example, overlapping HOIM images from two 90 degree rotationally offset illuminators and CD45 fluorescence (white blood cell control) at 4× were acquired from an unlysed human blood sample. Each cell event in the images were identified, fit to a 2-D Gaussian, and the integrated intensity of the signal for each cell was calculated. This was first done for the scatter information from one angle HOIM image and compared to CD45 fluorescence which shows white blood cells. It is clear that if the CD45 axis is ignored as would be required in label free measurements, the red blood cell cluster overlaps significantly with the white blood cell clusters. Multiplying the images from the two HOIM images with rotationally offset illuminators and then estimating the scatter signal (Y-axis, bottom) results in a downward shift in the scatter signal from red blood cells. This attenuation of the red blood cell signal moves towards better discrimination between white blood cells and red blood cells in the label-free scatter channel.

Further improvements could conceivably separate the white and red blood cell populations without the need for any fluorescent/absorption labels. It is worth noting that multiplying the two HOIM images resulted in more accurate white blood cell classification due to reduced partial volume effects and increased contrast to noise of white blood cells.

Another method to discard red blood cells from further analysis is to analyze the different illumination angle images separately and compare. For example, if all cells (white and red cells alike) are identified from one image and segmented or analyzed, that image region or analysis can be directly compared at the same locations in the image from another illumination angle. The actual image, pixel, or signal information can be directly compared for similarities by any number of standard methods. For example, mutual information of the image regions could be assessed to see if the image information is rotated or remains in the same location. Another example includes using structural similarity indices to assess how similar pixel intensities at corresponding locations compare. In our experience, white blood cells have a high similarity index between images from different illumination angles while red blood cells have similarity indices much lower. There are a number of methods for this that are publicly available. These similarity indices can also be used on fits that may be calculated for the image data, 2-dimensional Gaussians fit to the cell, for example. The metrics that define the fit or a set of pixels can also be compared. For example, the covariance matrix for the 2-dimensional Gaussian fit could be assessed for differences using the Euclidean distance or other distance metrics. One can imagine any set of available image analysis algorithms to compare the mutual or shared information between images of different illumination angles.

A final example embodiment includes using the information from multiple angle images to more accurately fit or segment white blood cells in the presence of red blood cells (by better identifying and fitting red blood cells). For example, in low magnification microscopy, white blood cells can be modeled as 2-dimensional Gaussians. However, these fits become inaccurate in the presence of red blood cells. Comparing mutual information or dissimilar information between images from two or more illumination angles could aid the fit to accurately converge to the proper cell location, shape, and intensity. This concept works for high magnification images to help rule out red blood cells from segmentation and analysis of white blood cells, a task that otherwise could be very challenging.

The scatter-based methods proposed here to analyze white blood cells in the presence of red blood cells requires little additional, low cost, optical instrumentation, no additional need for dyes or modifications to the existing instrumentation to attenuate the effect of red blood cells on the analysis of close-by white blood cells. This technology works for image-based cytometry in the low magnification regime where throughput is greatly increased compared to standard high resolution microscopy, and also for more standard high magnification microscopy (i.e. 0.5×-100×).

It is important to note that this technology is not limited to the analysis and discrimination of white blood cells and red blood cells. Utilizing directional scatter anisotropy could be useful in discriminating or better analyzing a number of cell and sample types. An example includes the discrimination of circulating tumor cells from red blood cells. Further example cells and biological structures whose analysis could benefit from this disclosure include any immune cell type, stem cells, fibroblasts, hepatocytes, gametocytes (malaria), exosomes and microvesicles, any form of cancer cells, epithelial cells, adipocytes, muscle cells, platelets, etc.

It is recognized that modifications and variations of the present invention will be apparent to those with ordinary skill in the art. It is intended that all such modifications and variations be included within the scope of the appended claims.

What is claimed is:

1. A method for distinguishing between red blood cells and white blood cells in a stationary blood sample including red blood cells and white blood cells, comprising:
    illuminating a blood sample that includes red blood cells and white blood cells with a first light, the first light forming a first oblique angle with respect to a detection axis extending longitudinally through a detector and the blood sample;
    illuminating the blood sample with a second light, the second light forming a second oblique angle with respect to the detection axis, and the second light being rotationally offset from the first light when viewed from a plane disposed above the blood sample, the plane being substantially perpendicular to the detection axis; and
    analyzing light side scattered by the first light and the second light from cells in the sample, and detected by the detector, to provide accurate discrimination of white blood cell types for white blood cell analysis based on a difference in a light scattering profile of the red blood cells as a function of the first light and the second light as compared to a light scattering profile of the white blood cells as a function of the first light and the second light,
    wherein the blood sample is stationary with respect to a field of view of the detector when illuminating the blood sample with the first light and when illuminating the blood sample with the second light, and the analyzing comprises combining information detected by the detector from light side scattered by the first light and the second light to determine a relative difference in isotropy/anisotropy of the red blood cells and the white blood cells.

2. The method of claim 1 wherein the difference in light scattering profile comprises scatter intensity of the red blood cells and white blood cells.

3. The method of claim 1 wherein the difference in light scattering profile results from different spatial locations within a cell that scatter the light.

4. The method of claim 1 wherein the difference in light scattering profile results for differences of polarization or phase of the scattered light.

5. The method of claim 1 wherein the first oblique angle is in the range of about 78 degrees to about 86 degrees, and the second oblique angle is in the range of about 78 degrees to about 86 degrees.

6. The method of claim 1 wherein the light has a wavelength anywhere in the ultraviolet-visible-near infrared electromagnetic spectrum.

7. The method of claim 6 wherein the wavelength is approximately 400 nm.

8. The method of claim 1 wherein a rotational offset angle formed by the rotational offset between the first light and the second light is in the range of about 75 degrees to about 105 degrees.

9. The method of claim 1 wherein a rotational offset angle formed by the rotational offset between the first light and the second light is in the range of about 50 degrees to about 120 degrees.

10. The method of claim 1 wherein a rotational offset angle formed by the rotational offset between the first light and the second light is in the range of about 45 degrees to about 135 degrees.

11. The method of claim 1 wherein the first oblique angle and the second oblique angle are substantially equal.

12. The method of claim 11 wherein the first oblique angle and the second oblique angle are in the range of about 78 degrees to about 86 degrees.

13. The method of claim 1 wherein illuminating the blood sample with light from the first light occurs prior to illuminating the blood sample with light from the second light.

14. The method of claim 1 further comprising counting white blood cells based on the discriminating of cell types as a function of the first light and the second light.

15. A method for distinguishing between two or more cell types in a stationary sample, comprising:
    illuminating a sample that includes two or more cell types with a first light, the first light forming a first oblique angle with respect to a detection axis extending longitudinally through a detector and the sample;
    illuminating the sample with a second light, the second light forming a second oblique angle with respect to the detection axis, and the second light being rotationally offset from the first light when viewed from a plane disposed above the sample, the plane being substantially perpendicular to the detection axis; and
    simultaneously analyzing light side scattered by the first light and the second light from the two or more cell types in the stationary sample, and detected by the detector, to discriminate the cell types based on a difference in light scattering profiles of the cell types, the difference in light scattering profiles of the cell types being a function of the first light and the second light,
    wherein the sample is stationary with respect to a field of view of the detector when illuminating the sample with the first light and when illuminating the sample with the second light.

16. The method of claim 15 wherein the difference in light scattering profile, as a function of the first light and the second light, is a relative difference in isotropy/anisotropy of the two or more cell types.

17. The method of claim 15 wherein the difference in light scattering profile is scatter intensity of the two or more cell types.

18. The method of claim 15 wherein the difference in light scattering profile results from different spatial locations within the two or more cell types.

19. The method of claim 15 wherein the difference in light scattering profile results from differences of polarization or phase of the scattered light.

20. The method of claim 15 wherein the first oblique angle is in the range of about 78 degrees to about 86 degrees, and the second oblique angle is in the range of about 78 degrees to about 86 degrees.

21. The method of claim 15 wherein the light has a wavelength anywhere in the ultraviolet-visible-near infrared electromagnetic spectrum.

22. The method of claim 21 wherein the wavelength is approximately 400 nm.

23. The method of claim 15 wherein a rotational offset angle formed by the rotational offset between the first light and the second light is in the range of about 75 degrees to about 105 degrees.

24. The method of claim 15 wherein a rotational offset angle formed by the rotational offset between the first light and the second light is in the range of about 50 degrees to about 120 degrees.

25. The method of claim 15 wherein a rotational offset angle formed by the rotational offset between the first light and the second light is in the range of about 45 degrees to about 135 degrees.

26. The method of claim 15 wherein the cell types are tumor cells and red blood cells.

27. The method of claim 15 wherein the first oblique angle and the second oblique angle are substantially equal.

28. The method of claim 27 wherein the first oblique angle and the second oblique angle are in the range of about 78 degrees to about 86 degrees.

29. The method of claim 15 wherein illuminating the sample with light from the first light occurs prior to illuminating the sample with light from the second light.

30. A method for distinguishing between two or more cell types in a stationary sample, comprising:
   illuminating a stationary sample that includes two or more cell types with a first light, the first light forming a first oblique angle with respect to a detection axis extending longitudinally through a detector and the sample;
   illuminating the stationary sample with a second light, the second light forming a second oblique angle with respect to the detection axis, and the second light being rotationally offset from the first light when viewed from a plane disposed above the sample, the plane being substantially perpendicular to the detection axis; and
   simultaneously analyzing light side scattered by the first light and the second light from two or more cells of the stationary sample disposed in a field of view of the detector at the same time to discriminate the two or more cell types of the stationary sample based on a difference in light scattering profiles of the cell types, the difference in light scattering profiles of the cell types being a function of the first light and the second light and the difference in light scattering profiles being a relative difference in isotropy/anisotropy of the two or more cell types.

31. The method of claim 30 wherein the first oblique angle is in the range of about 78 degrees to about 86 degrees, and the second oblique angle is in the range of about 78 degrees to about 86 degrees.

32. The method of claim 30 wherein a rotational offset angle formed by the rotational offset between the first light and the second light is in the range of about 45 degrees to about 135 degrees.

* * * * *